US006551250B2

(12) United States Patent
Khalil

(10) Patent No.: US 6,551,250 B2
(45) Date of Patent: Apr. 22, 2003

(54) TRANSIT TIME THERMODILUTION GUIDEWIRE SYSTEM FOR MEASURING CORONARY FLOW VELOCITY

(76) Inventor: Hassan Khalil, 15 Saad Zaghloul Square, 21511 Alexandria (EG)

( * ) Notice: Subject to any disclaimer, the term of this patent is extended or adjusted under 35 U.S.C. 154(b) by 0 days.

(21) Appl. No.: 09/819,425

(22) Filed: Mar. 29, 2001

(65) Prior Publication Data

US 2002/0177783 A1 Nov. 28, 2002

(51) Int. Cl.[7] ............................................... A61B 5/02
(52) U.S. Cl. ........................................ 600/505; 600/585
(58) Field of Search ........................... 600/433–435, 600/585, 900, 485, 486, 549, 505, 506, 507; 604/531, 532, 19

(56) References Cited

U.S. PATENT DOCUMENTS

| | | |
|---|---|---|
| 4,685,470 A | 8/1987 | Sekii et al. |
| 4,841,981 A | 6/1989 | Tanabe et al. |
| 4,979,514 A | 12/1990 | Sekii et al. |
| 5,046,505 A | 9/1991 | Sekii et al. |
| 5,056,526 A | 10/1991 | Khalil |
| 5,174,299 A | 12/1992 | Nelson |
| 5,509,424 A | 4/1996 | Al-Ali |
| 5,682,899 A | 11/1997 | Nashef et al. |
| 5,690,115 A | 11/1997 | Feldman et al. |
| 5,692,514 A * | 12/1997 | Bowman ................ 128/691 |
| 5,701,898 A | 12/1997 | Adam et al. |
| 5,797,398 A | 8/1998 | Bowman |
| 5,954,659 A * | 9/1999 | Curley et al. ............ 600/505 |
| 5,989,192 A | 11/1999 | Weijand et al. |
| 6,165,132 A | 12/2000 | Bowman |
| 6,287,292 B1 * | 9/2001 | Fariabi .................. 604/531 |

OTHER PUBLICATIONS

"Focus for the New Millenium: Diffuse Coronary Disease and Physiologic Measurements of Severity"; Morton J. Kern, Dept. of Internal Medicine, Division of Cardiology, St. Louis University Health Sciences Center, St. Louis, Missouri; ACC Current Journal Review, vol. 9, No. 2, Mar.–Apr. 2000, pp 13–19.

"Turbulence And Distributed Flow Patterns In the Circulation"; D.A. McDonald M.A., (Oxon), D.S., London, 1975; p 97.

"Blood Flow In Arteries"; D.A. McDonald M.A., D.M. (Oxon), D.S., London, 1975, p 98.

* cited by examiner

*Primary Examiner*—Henry Bennett
(74) *Attorney, Agent, or Firm*—Thomas R. Vigil; Welsh & Katz, Ltd.

(57) ABSTRACT

The system for measuring the velocity of blood flow in the coronary artery, comprises a guidewire adapted for coupling with conventional coronary intervention devices and has two or more temperature sensors mounted at equally spaced intervals along its distal segment. With the guidewire positioned at a point of interest in the artery, a steady infusion of a room-temperature saline solution is injected into the blood stream at the coronary ostium, lowering the local blood temperature slightly. Warmer pulsatile flow from the aorta mixes with this inflow, producing phasic temperature oscillations that are detected in sequence by the guidewire's temperature sensors. The elapse of time between the detected phase shifts indicates the velocity of the flowing blood. An external monitoring system connected to the guidewire provides instant read-outs of this value, which may be secured before, during and after intervention procedures, or after induced coronary hyperemia to determine coronary reserve.

20 Claims, 7 Drawing Sheets

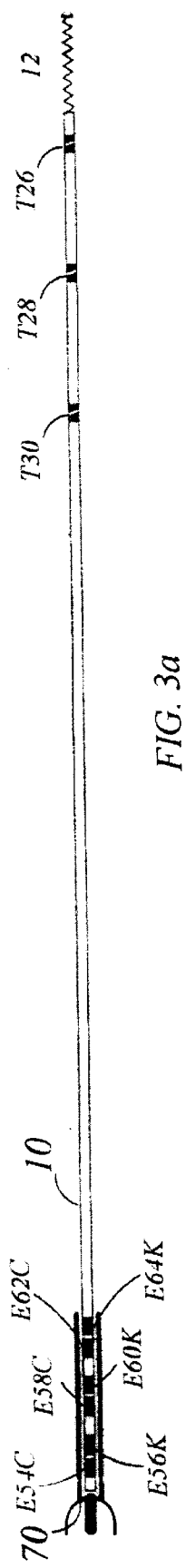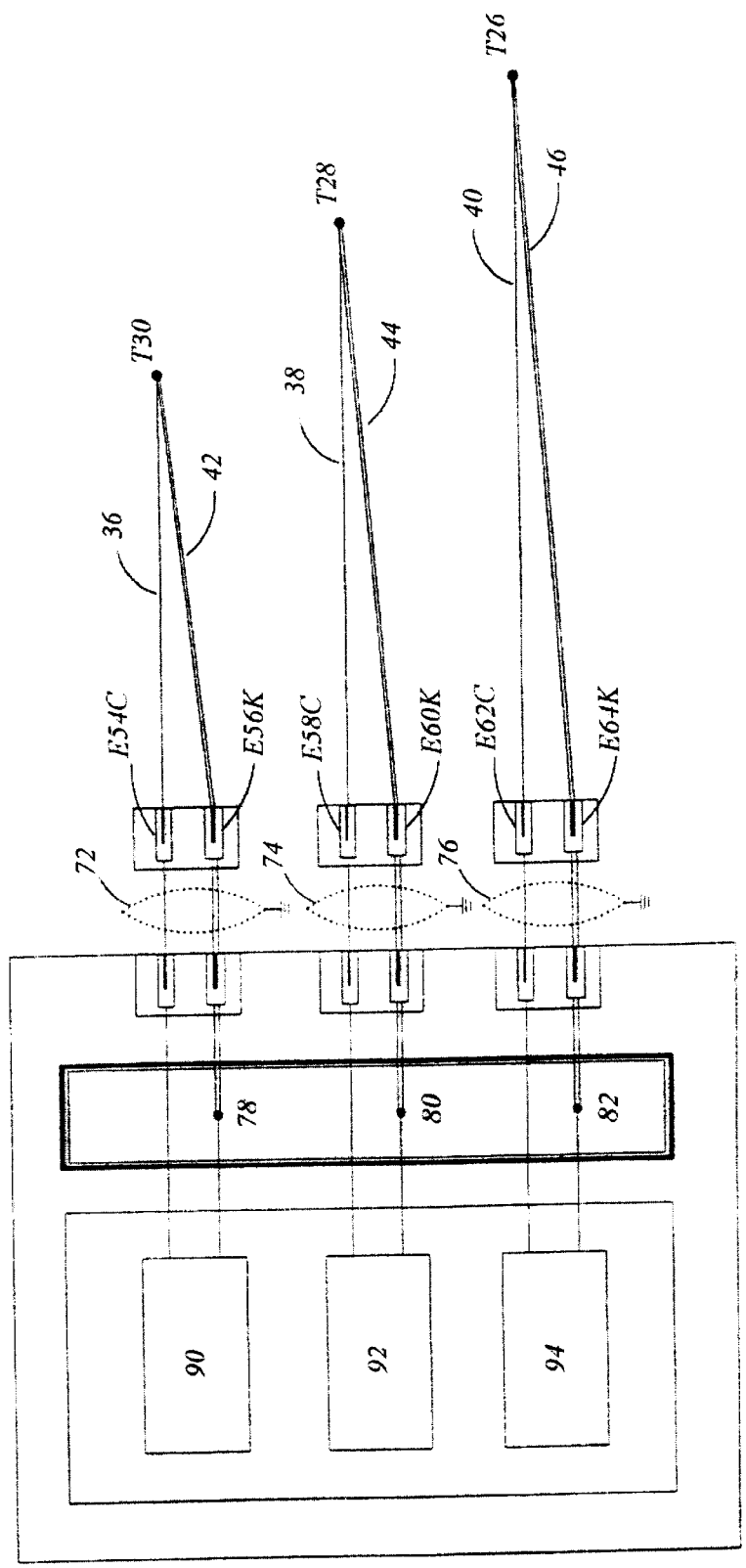
FIG. 3a
FIG. 3b

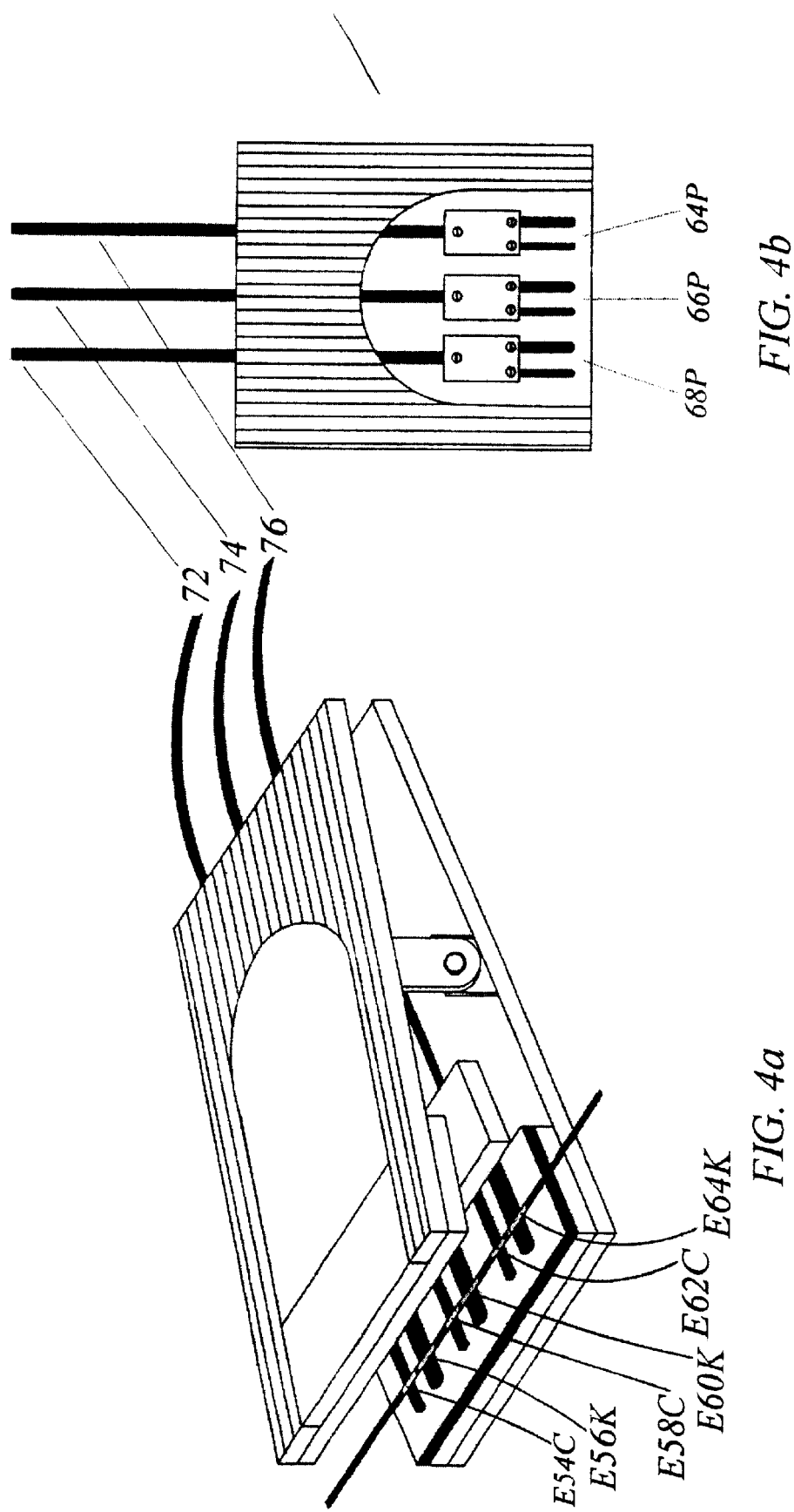

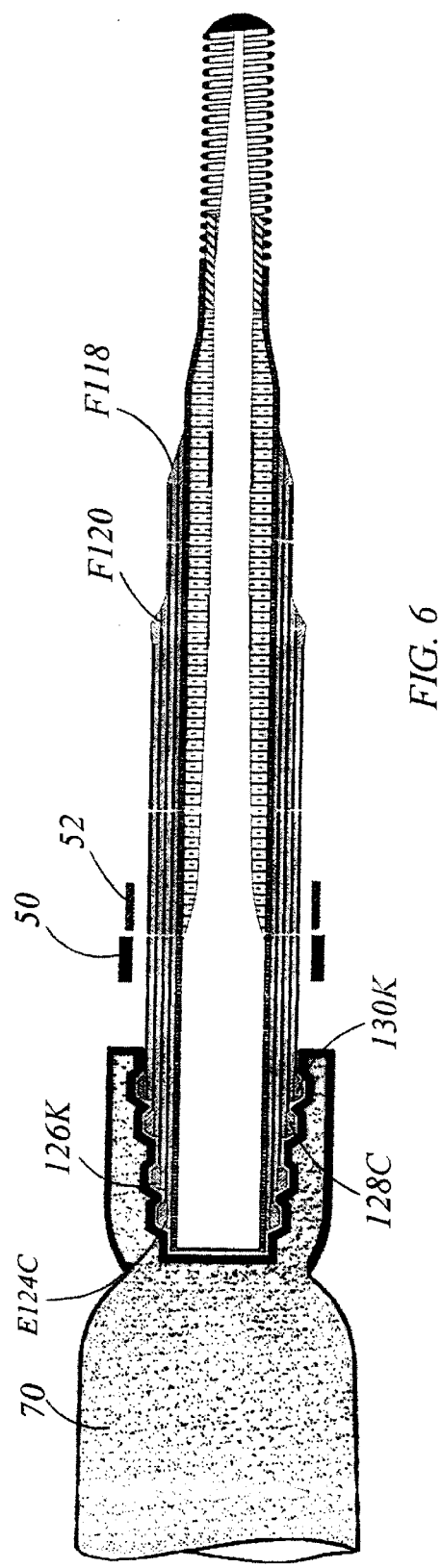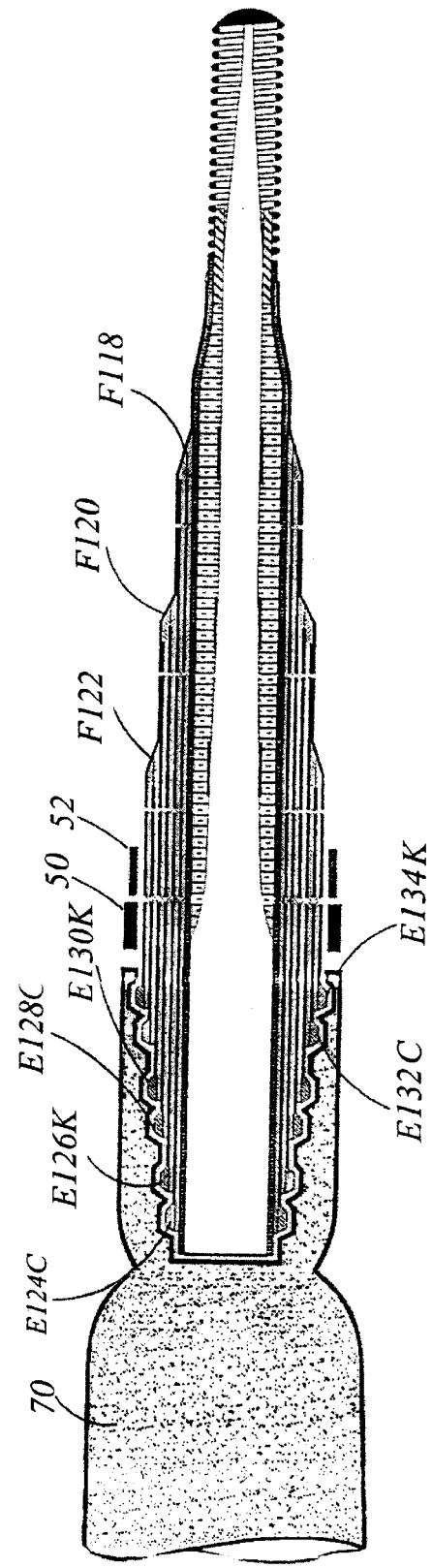

TRANSIT TIME THERMODILUTION GUIDEWIRE SYSTEM FOR MEASURING CORONARY FLOW VELOCITY

BACKGROUND OF THE INVENTION

1. Field of the Invention

The present invention generally relates to intravascular medical devices used to measure blood flow velocity. More specifically, the present invention relates to intravascular diagnostic devices used to evaluate the state of coronary blood flow and velocity at basal conditions and after induced coronary hyperemia as well as the early and late outcome of coronary intervention procedures. The present invention represents a significant advance in the state of the art. Among other advantages, it offers high degrees of accuracy, safety, and speed of use, cost-to-benefit value and the potential for wider application in other cardiovascular fields.

2. Description of the Prior Art

Measurement of coronary flow velocity and coronary reserve have gained wide acceptance as crucial diagnostic values in the decision-making process for coronary angioplasty and other cardiac intervention procedures. Following the rapid progress in the quantities of angiography (QCA) achieved during the 1980s, it was hoped that anatomic information alone, enhanced by digital techniques, would become so comprehensive that there would be no further need for physiological confirmation of angiographic data. To date, however, QCA has not fulfilled its promise to predict the physiological significance of coronary artery stenosis or to quantify increases in artery flow following angioplasty.

At present, these parameters are evaluated most commonly by insertable coronary instruments such as Doppler guidewires or pressure measuring guidewires. A more recent invention describes a new guidewire that includes both pressure and flow sensors. While these methods have achieved reasonable degrees of accuracy, they all pose certain limitations whether in terms of cost, ease of use or speed in obtaining results.

Coronary flow measures have also been measured by X-ray densitometry, which is based on the mean transit time of a contrast medium between a proximal site and a distal site of the vessel. The application of this measurement technique to the coronary artery is complicated by technical problems arising from the continuous motion of the coronary artery, requiring manually positioned windows for the video-densitometric measuring device. In addition, determination of the front velocities of the contrast medium required in repeated injections by means of an ECG triggered power injector, during three to five phases of different cardiac cycles and their reconstruction to provide the flow rate pattern of a single cardiac cycle.

Thermodilution has long been a promising technique in the study of circulation. To prove its reliability in the determination of blood flow and velocity, Fegler in 1957 obtained simultaneous thermodilution curves from two catheter-mounted thermal sensors at the arch and bifurcation of the aorta by injecting room temperature saline solution into the right atrium.

More recently, Weijand et al. (U.S. Pat. No. 5,.989,192, Nov. 12, 1999) measured cardiac output by positioning a device with two closely spaced thermal sensors in the ascending aorta to detect spontaneous cyclic temperature variations during the cardiac cycle.

These spontaneous cyclic temperature variations do not extend to the coronary blood flow, as they merge and dissipate through the swirling motion of blood in the coronary sinus behind the opening aortic valve leaflet leading to vortex generation before the ostium of each coronary artery.

In addition, the mainly diastolic nature of coronary blood flow further dissipates these spontaneous temperature variations leading to a steady temperature baseline in the coronary circulation.

Examples of analogous and non-analogous prior art blood flow velocity measurement systems are disclosed in the following U.S. Patents.

| U.S. Pat. No. | Patentee |
| --- | --- |
| 4,841,981 | Tanabe et al. |
| 4,685,470 | Sekii et al. |
| 4,979,514 | Sekii et al. |
| 5,046,505 | Sekii et al. |
| 5,056,526 | Khalil |
| 5,174,299 | Nelson |
| 5,509,424 | Al-Ali |
| 5,517,989 | Frisbie et al. |
| 5,682,899 | Nashef et al. |
| 5,690,115 | Feldman et al. |
| 5,692,514 | Bowman |
| 5,701,898 | Adam et al. |
| 5,797,398 | Bowman |
| 5,989,192 | Weijand et al. |
| 6,165,132 | Bowman |

However, thermodilution techniques have rarely been applied to diagnostics of the coronary arteries. The present invention represents both a significant refinement of tested thermodilution techniques, and a promising new method for measurement of coronary velocity and flow.

SUMMARY OF THE INVENTION

The present invention is a potentially cost effective intravascular guidewire system that is capable of quickly and accurately measuring coronary flow velocity and coronary reserve. The device generates these parameters by establishing the transit time of a thermal signal as it passes downstream with the coronary artery blood flow.

The proposed thermodilution guidewire includes an elongated shaft with a floppy tip that is inserted into a segment of interest in the mammalian coronary arteries for purposes of guiding an intervention catheter, scope or other medical device. The preferred embodiment includes several thermal sensors, three of which are described in the present embodiment, consisting of thermocouple measuring junctions, mounted in sequential order at equal predetermined intervals along the terminal segment of the guidewire shaft, at a distance of 10, 25 or 50 mm, proximal to its spring tip. Two respective insulated electrical paths of the same materials as the thermal junctions extend from each thermocouple in a helical winding along the length of the guidewire shaft to its proximal end, where each electrical path is joined to one of six separate sleeve electrodes. The shaft and its added components are sheathed in an insulating material suitable for smooth introduction into a human vessel.

Each of the six sleeve electrodes located at the guidewire's proximal end is electrically connectable through external cables to its respective reference junction that is maintained at a constant temperature medium. The electrodes are also electrically connected to three separate thermocouple amplifiers, a fast sweep multiple channel color coded monitor, an online programmed computer and a printer.

When the thermodilution guidewire has been positioned at the segment of interest of the coronary artery, an upstream thermal indicator is introduced at the ostium of the coronary artery in the form of a steady, slow infusion of room temperature saline at 22 degree centigrade over 10–15 second period. This infusion is similar to the standard procedure of flushing a guiding catheter with room temperature saline during coronary interventions.

Mixing of room temperature saline infusion with coronary blood flow induces a transient temperature gradient during the period of infusion. The relatively warmer coronary flow, with its pulsatile phasic pattern of small systolic and large diastolic components, thus acts as a warm thermal indicator that reflects the degree of thermodilution. This degree changes during each phase of coronary flow, creating periodic oscillations of the temperature gradient that simulate rectified sine waves.

Each temperature oscillation is sequentially detected by the three serially mounted thermal sensors as three consecutive rectified sine waves with a phase shift between them. The degree of phase shift between consecutive waves is an expression of the transit time of blood flow between sequential thermal sensors. This value which is inversely related to the average phasic velocity is directly determined by an online computer programmed to calculate the average flow velocity from the transit time between successive phase shifts. An online multiple channel color coded monitor with adjustable sweep velocity also displays these successive oscillations during the measuring time. The monitor's sweep velocity may be increased to match the fast average phasic velocity met with during measures of fast flow velocity of coronary reserve, and calibrated to give a real-time direct digital readout of these values.

The system can determine values for coronary flow volume when the angiographically measured diameter of the segment of interest of the coronary artery is supplied to the computer. The present invention may also determine coronary reserve, which is of particular value during decision making in cases with intermediate coronary stenosis, as well as in determining the immediate and late results of intervention procedures. For the device to determine coronary flow reserve, the value for blood flow velocity is first obtained at basal conditions, and then after inducing maximal coronary flow hyperemia. In addition, the rate of return of the trailing end of temperature drop to its original baseline level provides an indirect evaluation of transmyocardial flow velocity.

The transit-time guidewire described in the present invention may also be modified to suit the size and flow velocity of the cerebral carotid, renal and other peripheral arteries to provide valuable data on flow velocity and reserve in these vessels.

BRIEF DESCRIPTION OF THE DRAWINGS

FIG. 3a is a side plan view of the guidewire showing serially mounted thermal sensors at the side of the radio opaque markers, a spring tip on the distal segment, and six sleeve electrodes on the proximal segment.

FIG. 3b is a schematic circuit diagram of the thermal sensors showing the successive position of the three thermal sensors, their associated sleeve electrodes, three thermocouple connectors, three external cables, three reference junctions and three thermocouple DC amplifiers.

FIG. 4a is a perspective view of a clamp connector which is located at the proximal end of the guidewire and shows three spring clamp thermocouple connectors electrically connected to respective copper and constantan electrodes mounted on the guidewire.

FIG. 4b is a top plan view of the thermocouple connectors shown in FIG. 4b.

FIG. 6 is a cross-sectional view of one embodiment of the guidewire system, wherein the circuitry of helically coiled wires shown in FIG. 1 is replaced by alternating layers of copper and constantan films with insulating ink film between them and with one interval between two thermal sensors.

FIG. 7 is a cross-sectional view of another embodiment of the guidewire system wherein the circuitry of helically coiled wires shown in FIG. 1 is replaced by alternating layers of copper and constantan films with insulating ink film between them and shows two intervals between three thermal sensors.

DESCRIPTION OF THE PREFERRED EMBODIMENTS

Figure 1B:
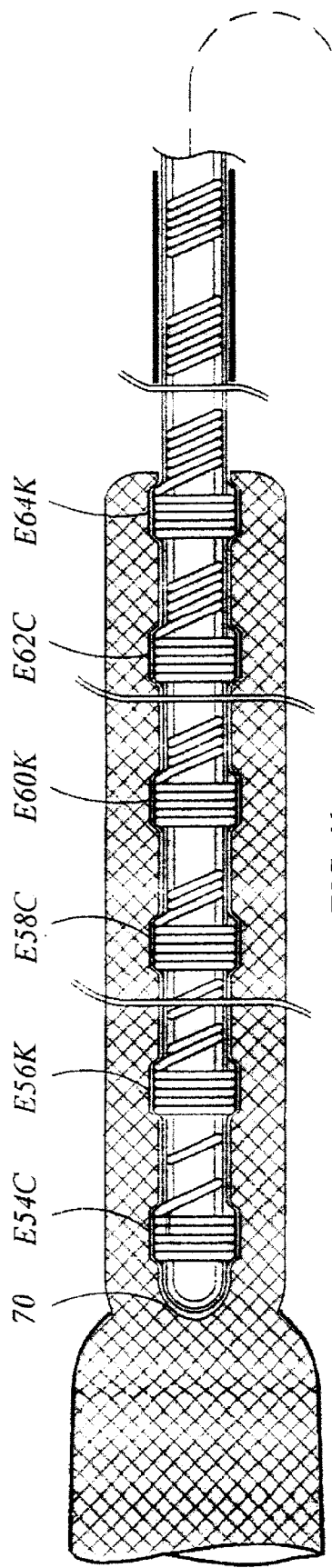
FIGS. 1a and 1b are an enlarged side elevational view illustrating (a) the distal segment of the guidewire and its radio opaque spring tip, showing three sequentially positioned thermal sensors with helically wound wires leading from them to (b) the proximal segment of the guidewire showing six sleeve electrodes.

The following description should be read with reference to the attached drawings, in which like elements are numbered identically. Where specific materials, dimensions, manufacturing processes and techniques for usage are described, those skilled in the field of the invention will recognize them as exemplary. However, suitable alternatives may also be utilized.

The Measuring Device and its External Connections

As shown in FIG. 1, the preferred embodiment of the present invention comprises an insulated elongated guidewire shaft 10 measuring about 70 inches (180 cm) long and 0.008 inches (0.20 mm) outside diameter (O.D.) Of spring steel wire or an alloy with a degree of flexibility and steerability that is suitable for a coronary artery intervention guidewire. A distal segment of about 1.3 inches (3 cms) in length is tapered to about 0.003 inches (0.075 mm) O.D. A radio opaque spring coil 37 (FIGS. 1 and 3) surrounds this distal segment and is attached at both of its ends to the guidewire shaft by welding or soldering as indicated at 14 and 16.

In the preferred embodiment, three radio opaque reference markers 18, 20 and 22 (FIGS. 1 and 3), each about 2 mm wide, are affixed at equal intervals of 15, 25 or 50 mm along the distal segment of the guidewire shaft 10, beginning at a distance of about 5 to 10 mm proximal to its spring tip 12. This segment of the guidewire shaft is then coated to a thickness of about 0.0008 inch (0.020 mm) with a flexible medical grade adhesive polymer coating to serve as an electric insulating spacer 24 (FIG. 2).

Figure 1A:
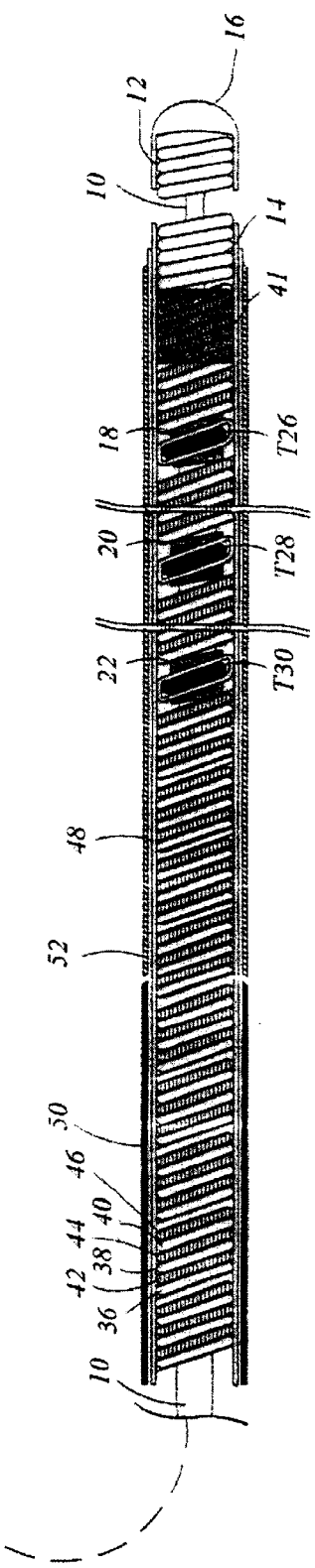
Figure 2:
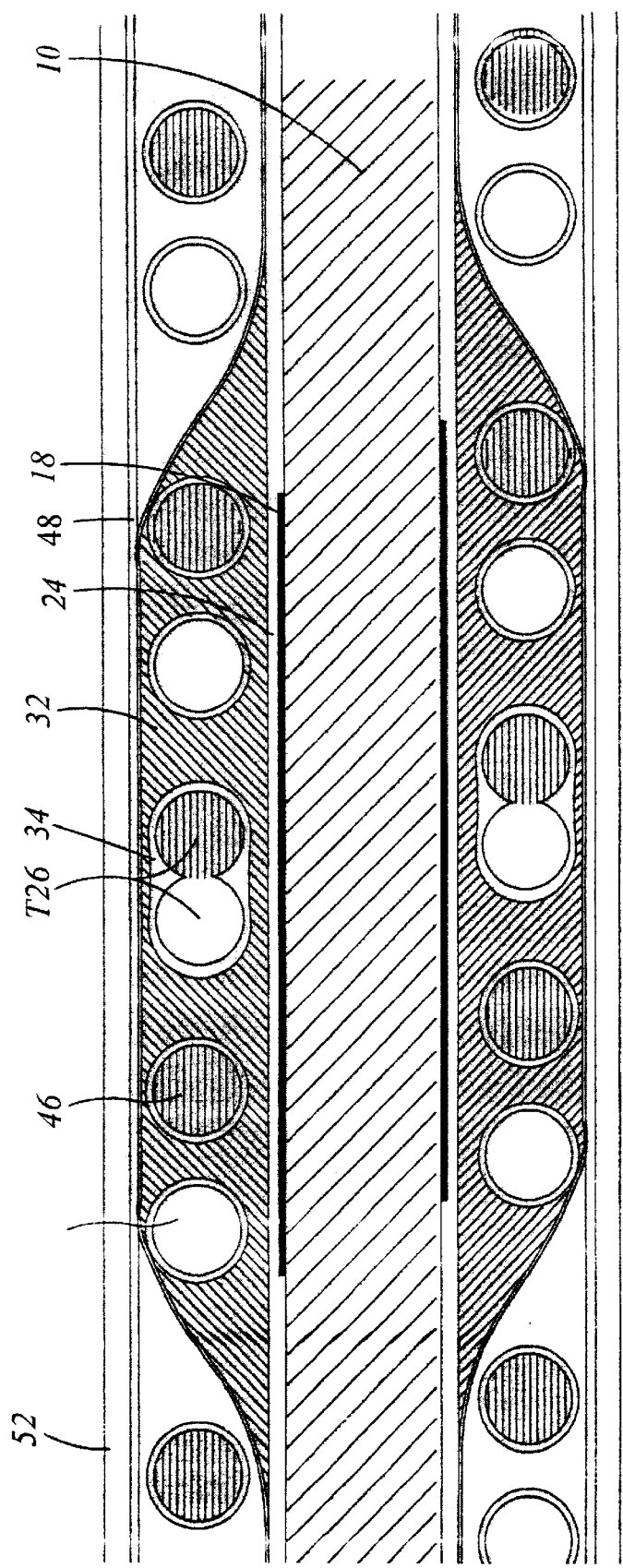
FIG. 2 is an enlarged longitudinal sectional view illustrating one of the flattened thermal sensors shown in FIG. 1 and shows the positions of a radio opaque marker along the guidewire shaft and of insulating materials.

Three thermal sensors T 26, T 28 and T 30 (FIGS. 1, 2 and 3) are mounted over this insulating material 24 at the sites of the equally spaced radio opaque markers 10, 11 and 12, using an adhesive epoxy 32 (FIG. 2). In the preferred embodiment, each of the three thermal sensors comprises of a flattened thermal measuring junction of copper-constantan thermocouple (Type T). These miniature thermal sensors do not obstruct the flow in small vessels and are considered ideal for measuring changes in localized body areas. Their extremely small mass provides an accurate, fast response thermal sensor that is not affected by pressure changes.

The thermal sensors may be formed by fusing, electron beam welding or simply by soldering together the two adjacent wires with a high quality solder, conductive silver ink or silver epoxy to form a common junction 34 (FIG. 2). This soldering joint should preferably extend for about 2 to 3 mm along the two adjacent wires, to cover the wires' circumferential winding around the thermally and electrically insulated stainless steel wire shaft 10 and radio opaque marker 12 (FIG. 2). The high thermal conductivity of silver-containing solder helps to convey the average temperature level around the guidewire to the site of the thermal sensor common junctions. For an enlarged view of one of these thermal junctions, showing its placement over a radio opaque marker, the application of insulating materials and the circumferential winding of the wires jointed at the thermal junction, refer to FIG. 2.

Two insulated conductor lead wires, measuring 0.0016 inch (0.04 mm) O.D., of copper 36, 38 and 40 and constantan 42, 44 and 46 in FIG. 1*a* (40 and 46 are also shown in FIG. 2) extend from each thermal junction as adjacent helical coils which spiral the length of the guidewire shaft 10. In the preferred embodiment, the guidewire shaft and the helical lead wires 36–46 are first coated with two thin layers of medical grade polymer 24 and 48 (FIGS. 1 and 2), starting beyond the proximal sleeve electrodes and ending before the distal segment. Coating the helical coil wires levels out the grooves between the wires. More importantly, this coating, fortified by the helical lead wires, acts as a thin tube, adding pushability and steerability to the thin guidewire shaft. The proximal segment is then coated with a close fit insulated hypotube or sheath with a wall thickness less than 0.0015 inch (0.04 mm) 50 (FIGS. 1*a*, 6 and 7), and extending as a thin hydrophilic, silicone or a polytetrafluoroethylene (PTFE) coating over the distal, more flexible section 66 (FIGS. 1*a*, 6 and 7). Sliding a hypotube 65 over the proximal section offers further protection to the helical lead wires by reducing their exposure to damaging abrasions, and provides additional pushability and steerability for advancing the guidewire into the coronary vasculature. The distal flexible coating provides a smoothly gliding surface over the distal segment of the guide-wire shaft carrying the helical lead wires and the three thermal sensors.

The lead wires 36–46 terminate at the proximal 15 cm end segment of the guidewire shaft as three paired electrodes of copper and constantan E 54 C and E 56 K, E 58 C and E 60 K, and E 62 C and E 64 K (FIGS. 1, 3*a* and 4). In the preferred embodiment, these electrode pairs take the form of sleeve electrodes as shown in FIGS. 4*a* and *b*, with each pair spaced to match a prospective clip-on electrode connector plates 64P, 66P and 68P (FIG. 4*b*). An alternative type of electrode connector 70, with a cylindrical receptor that would allow freer steering of the guidewire, is envisaged in FIGS. 1*b*, 3*a*, 6 and 7.

The six sleeve electrodes E 54 C and E 56 K, E 58 C and E 60 K, and E 62 C and E 64 K are externally connectable through extension cables 72,74 and 76 (FIGS. 3*b* and 5) to three respective reference junctions 78, 80 and 82 (FIG. 3*b*) that are maintained at a constant temperature medium.

Figure 5:
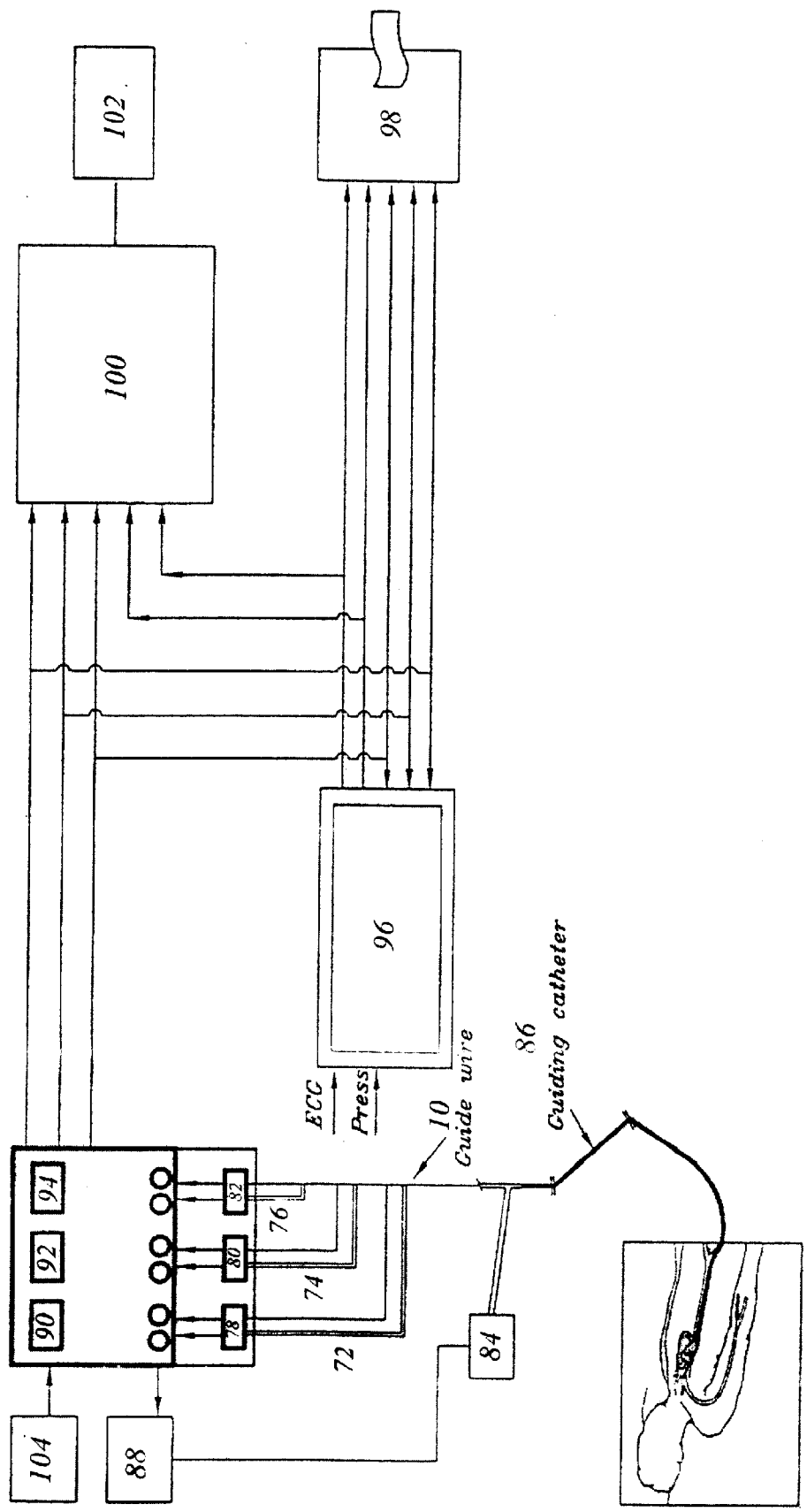
FIG. 5 is a schematic circuit diagram illustrating the external components that comprise the measuring system of the present invention and shows how a guiding catheter is introduced through the femoral artery of a recumbent patient until the ostium of the coronary artery, with a saline infusion pump connected to the external proximal segment of the guiding catheter.

Further external connections of the device are illustrated in FIG. 5. These include a servomotor-driven infusion pump 84 which feeds into the guiding catheter 86 used to position the guidewire within the coronary artery. The pump is adjusted to inject a slow steady infusion of 1–3 ml/sec room temperature saline at the ostium of the coronary artery over a period of 10–15 seconds. The external connections of the device preferably should also include a manual or automatic feedback circuit 88 to adjust the rate of saline or other miscible infusion so as to produce a standard average temperature gradient, whether at basal conditions or during measures of coronary flow reserve.

Output from thermal sensors T 26, T 28 and T 30 (FIG.1) and their reference junctions 78, 80 and 82 (FIG. 3*b*) is transmitted to three separate thermocouple amplifiers 90, 92 and 94 (FIGS. 3*b* and 5), a high speed color-coded monitor 96 (FIG. 5), a recorder 98, and an online programmed microprocessor, or computer 100 with its associated printer 102. The computer should be programmed to calculate various values derived from the measured transmit time of coronary blood flow passing between each pair of thermal sensors, according to the formulae described below. A push button, electronically calculated standard 104 serves to calibrate the temperature gradient induced by the saline infusion.

Method of Use

Ideally, electrocardiographic, intra-aortic pressure and blood pressure tracings, as well as the patient's breathing, should be continuously monitored throughout the procedure described below.

In the preferred embodiment, the thermodilution guidewire is introduced through a Judkin's guiding catheter 86 (FIG. 5) into the ostium of the coronary artery, and the guidewire's distal segment is steered forward through the coronary branch of interest. If there is a segment with suspected coronary stenosis, the flexible radio opaque spring tip of the guidewire 37 is gently manipulated through this segment and pushed forward for 3–5 cms to reach the distal coronary branches.

Baseline temperature level of blood flow through the coronary artery is first detected by the three sequentially mounted thermal sensors T 26, T 28 and T 30, which are electrically connected to their three respective D.C. amplifiers 90, 92 and 94. Output from these amplifiers appears as three separate tracings on the color monitor 96, which should preferably be a fast-sweep monitor with adjustable speed up to 1000 mm/sec. A manual or automatic zero suppress adjusts the three readings closer together. Use of the push button predetermined standard 104, which is connected online with the three thermal sensor amplifiers, produces a standard deflection equivalent to 0.1–1.0 degrees centigrade below baseline temperature level of coronary blood flow.

Utilizing the constant rate perfusion pump 84 connected to the guiding catheter 86, a slow, steady rate perfusion of room temperature (approximately 22 degrees C.) normal saline or Ringer's solution is started at 0.5–2.0 ml/sec and continued for 10–15 seconds according to the request of the operator. This constant rate saline infusion flows from the tip of the guiding catheter at the coronary ostium into the coronary artery at a temperature about 12–15 degrees centigrade below that of the coronary blood flow. Mixing between the steady, slow saline infusion and the phasic, pulsatile flow of the coronary blood induces a temperature gradient within 0.5 degree centigrade that flows downstream to the distal epicardial coronary branches at the same velocity as coronary blood flow.

Rhythmic changes of the phasic pulsatile coronary blood flow with each phase of the cardiac cycle modulate the degree of thermodilution induced by the steady slow infusion, creating periodic oscillations of temperature gradient. These oscillations that are produced by the characteristic biphasic coronary flow pattern with its large diastolic and small systolic components, simulate rectified sine waves, as illustrated by TW 26, TW 28 and TW 30 in FIGS. 8, 9 and 10. These cyclical temperature changes reflect the different degrees of dilution of the cool saline infusion in the relatively warm coronary blood during the different phases of the cardiac cycle with the less diluted diastolic phase producing warmer temperatures than that of the more fully diluted systolic phase. The size of these waves do not affect the accuracy of the proposed method, since the method is based on the transit time of the phase shift between successive waves as detected by the sequentially located thermal sensors. In addition, the length of intervals between the diastolic and systolic components provides a useful indication of the relative size of the two components.

Each phase of the simulated rectified sine waves of temperature gradients is detected in sequence by the three serially mounted thermal sensors T 26, T 28 and T 30 as it arrives at the site where the sensor is mounted. In normal coronary flow, these waves are expressed as three consecutive rectified sine waves FIG. 8, with two equal transit times between them expressed as phase shifts. The degree of phase shift between recorded waves is an expression of the transit time of the average flow velocity of coronary flow at the time of measurement.

$$V = \frac{\Delta S}{\Delta T}$$

Where V=velocity, S=the distance between each pair of thermal sensors, and T=transit time.

Using this formula the online computer 100 generates the mean blood flow velocity during a single cardiac cycle. Since room temperature infusion extends over a predetermined measuring time of 10–15 seconds covering several cardiac cycles, the average flow velocity during the measuring procedure is also determined. Values of volume flow may be calculated when the angiographically determined vessel diameter is supplied to the online programmed microprocessor according to the following equation:

$$Q = \frac{\Pi}{4} \times D \times \frac{\Delta S}{\Delta T}$$

Where Q is calculated when the diameter D is measured by angiography.

The thermal time constant of the fast response thermal sensors in a running fluid medium such as the bloodstream is less than 20 milliseconds. This thermal time constant affects all the consecutive oscillations equally and therefore has no effect on the transit time of the phase shift between them. Thorough mixing of the infused saline and the coronary flow is not essential since it is the transient time between identical phases and not the degree of temperature gradient which is of crucial value. Similarly, insignificant thermal conduction through the arterial walls does not affect the transit time of temperature changes.

Figure 8:
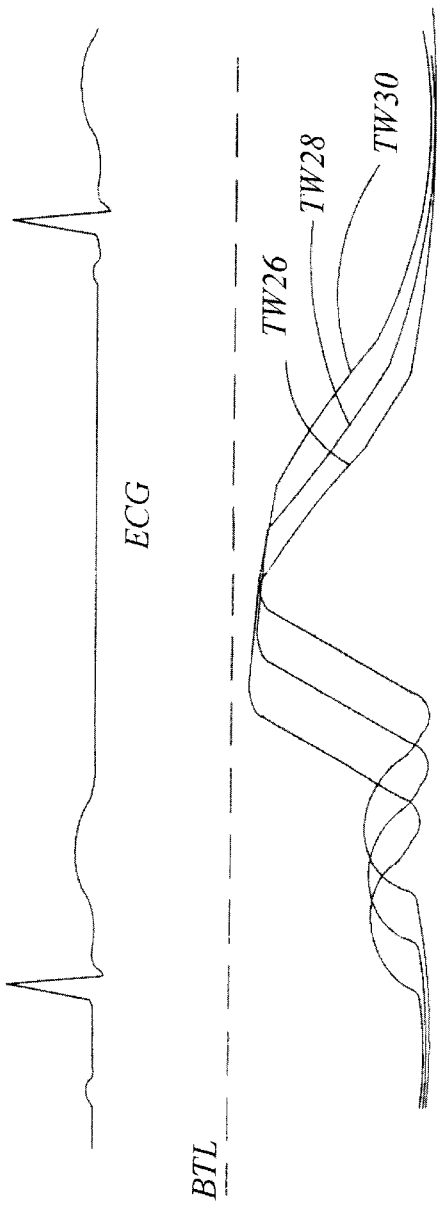
FIG. 8 is a graph of an ECG waveform above one of three predicted ranges of biphasic temperature wave shifts as detected by three serially mounted temperature sensors under different conditions.

Determination of coronary flow reserve may be carried out by repeating room temperature saline infusion after increasing the rate of coronary flow by means of pharmacologically-induced maximal dilatation of the coronary arteries. Under basal conditions normal coronary flow velocity induces a standard range of transit time between consecutive waves, and is accurately calculated from the degree of phase shift between consecutive waves (FIG. 8). During measures of coronary flow reserve, the increased flow velocity produces narrow phase shifts denoting short transit times. The degree of narrowing is inversely proportional to the size of coronary flow reserve.

Figure 9:
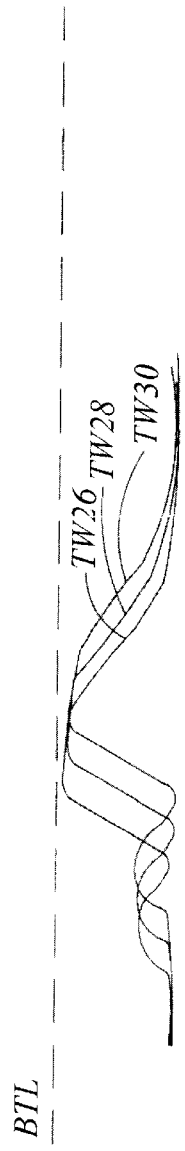
FIG. 9 is a graph of another one of three predicted ranges of biphasic temperature wave shifts as detected by three serially mounted temperature sensors under different conditions.

Referring to FIG. 9, the increased rate of coronary flow is also expressed by smaller temperature gradients, since the infused saline is diluted in the increased volume of coronary flow reserve.

Figure 10:
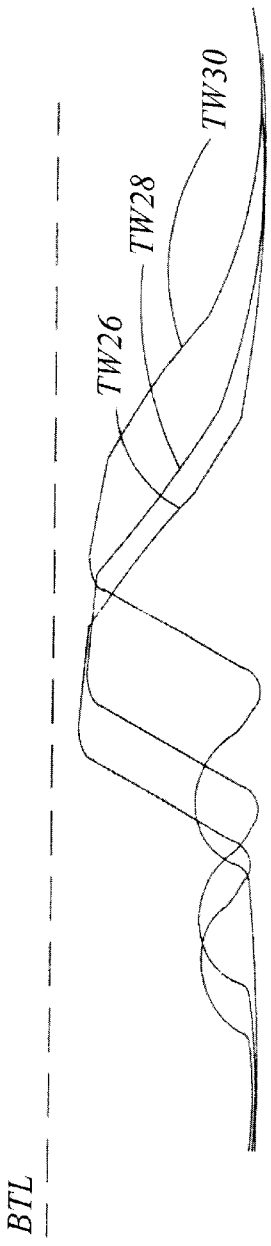
FIG. 10 is a graph of third one of three predicted ranges of biphasic temperature wave shifts as detected by three serially mounted temperature sensors under different conditions.

Post stenotic reduction of the mean velocity prolongs the transit time between successive waves and is expressed by widening of the phase shifts between them (FIG. 10). Evaluation of the degree of coronary stenosis which is a valuable parameter in decision making is determined by the degree of widening of the phase shift at basal conditions and during measures of coronary reserve. For optimal patient care, this procedure may be repeated to evaluate the immediate and late outcome of coronary intervention.

The forward direction of coronary flow is indicated by the order of colors shown on the color coded monitor 96. The order of colors would be reversed in certain types of coronary stenosis with reversed flow from adjacent collateral vessels.

After the saline infusion is stopped, the trailing part of the transient temperature drop with its characteristic rectified sine wave pattern returns either gradually or rapidly to its original straight baseline level. The rate of its return to its original baseline level is an indication of the transmyocardial flow velocity, which may reveal functional or structural alterations in the microvascular circulation.

Suggested Refinements and Alternate Embodiments

FIG. 1 illustrates that copper and constantan lead wires 36–46 may also extend beyond the thermal sensors T 26, T 28 and T 30 to distally in a continued helical coil winding until the beginning of the spring tip 12. These extensions of the helical coil lead wires beyond the thermal sensors serve to maintain the smooth surface of the distal segment of the guidewire, which will assist easy introduction of the guidewire through the distal branches of the coronary artery. In addition, these distal extensions may help to secure the thermal sensors in position during the winding process. The extensions have no electric function and do not interfere with the function of the thermal sensors. After the thermal sensors and adjacent wires leads have been fixed to the insulated stainless steel shaft, the distal extensions may be electrically interrupted by any cutting instrument. The terminal comprising 3 mm of these helical coils and the proximal end of the radio opaque spring tip may be fixed to the guidewire shaft with an anchor ring 40 (FIG. 1) of epoxy resin or Polytetrafluoroethylene (PTFE).

The foregoing description of the preferred embodiment of the present invention applies to a guidewire with two intervals between three thermal sensors. The advantage of having two intervals is to allow simultaneous comparative measures along both intervals. A simple guidewire designed on the same principles but with a single interval separating two thermal sensors, could be less expensive to manufacture, but would not provide two simultaneous measures, rendering it less useful for comparative studies.

It is envisaged that a more complex guidewire could comprise three intervals between four thermal sensors. By positioning the proximal interval before and the distal after a stenotic lesion, this configuration would provide the advantage of determining simultaneously the blood flow velocity both proximal from and distal to a coronary stenotic segment. The middle interval could provide further information about the velocity of blood flow through the stenosed segment.

In the preferred embodiment of the present invention, Type T copper and constantan thermocouples are used as thermal sensors. Other types of thermal sensors may be used when preferred. A significant advantage of using thermocouples is that they require no electric current to be introduced along the lead wires. This is an important consideration, given the unpredictable flow velocity which a stenosed segment of the coronary artery may experience, and its sensitivity to the heat generated by the electric current utilized by other types of thermal sensors. Alternate types of thermal sensors may take the form of thin film of platinum foil, or of suitable sized thermistors configured as resistor thermal sensors over one arm of a three lead thermometer bridge.

In the description of the preferred embodiment of the present invention, the most distal of the three sequentially mounted thermal sensors is located just proximal to the terminal radio opaque spring copil. When desired, this thermal sensor may be placed at the tip of the radio opaque spring coil (not shown). This location of the distal thermal sensor at the extreme tip of the guidewire offers the advantage of providing values of average flow velocity along more distal coronary branches and collateral vessels, but it may limit the guidewire's much-needed high degree of flexibility.

It is further contemplated that the helical coils of the thermal sensor lead wires described in the preferred embodiment could be replaced with different types of coated conductor paths of the same thermocouple materials running the length of the guidewire shaft. FIGS. 6 and 7 illustrate one type of alternative conductor paths applied to both two and three sensor configurations of the device. In this version, alternative successive copper and constantan conductor film coatings would be painted, sprayed or printed over an insulated guidewire shaft. Each conduction film would be insulated from the next by a thin film of insulating ink, except at both ends of the conductor film, where they would form sequentially placed thermal sensors at the guidewire's distal segment F 118, F 120, F 122 and sleeve electrodes E 124C, E 126K, E 128C, E 130K, E 132C, E 134K at its proximal segment. Assuming each of the conductor films and their insulating layers do not exceed 0.01 mm, they would have a total thickness of 0.06 mm adding 0.12 mm on both sides of an insulated guidewire shaft about 0.15 mm O.D. giving a total thickness of 0.27 mm. A close fit thin coating of 0.04 mm thickness 65 giving a total thickness of 0.35 mm (0.014 inch) to the guidewire, would protect these films over most of their length, except the distal 25 mm segment, where the hypotube would be extended as a thin flexible polymer coating 66. If practicable, this arrangement would offer considerable advantages in ease of manufacturing.

I claim:

1. A system for measuring the velocity of blood flowing in a coronary blood vessel, said system comprising:

a guidewire adapted for coupling to a conventional device that is used during coronary intervention procedures, said guidewire comprising an elongated guidewire shaft having flexibility, pushability and steerability for use in coronary intervention procedures;

at least two temperature sensitive elements each comprising a temperature sensor mounted along a distal segment of said elongated guidewire shaft:

said temperature sensors being disposed at equally spaced intervals over said distal segment of said guidewire shaft;

means for measuring the velocity of coronary blood flow with said temperature sensors, when said distal segment is positioned within a coronary blood vessel, by detecting in sequence the fluctuating thermal signal produced by changing the thermal energy level of the coronary blood stream as it flows in the vessel;

said measuring means comprising:

means for changing the thermal energy level of the coronary blood stream by introducing a slow infusion of solution, having a temperature different than the temperature of the blood and being miscible with blood, into the coronary blood vessel, said infusion being introduced upstream at the coronary ostium and being carried downstream to induce a transient temperature difference in the coronary blood stream of a fraction of a degree centigrade, and whereby said temperature difference is interrupted by the phasic oscillations generated by pulsatile blood flow entering from the aorta; and, means for measuring the time interval between said phasic oscillations by detecting in sequence with each one of said thermal sensors the pattern of temperature fluctuation of the blood at different locations in the blood vessel, as it flows in the coronary blood vessel, and for producing a value for said time interval which is indicative of the velocity of the blood flow in the coronary blood vessel.

2. The guidewire of claim 1, wherein each of said temperature sensors comprises a thermocouple measuring junction which is placed on top of radio opaque markers and over an electrically and thermally insulated segment of said guidewire shaft.

3. The system of claim 1, wherein said solution has a temperature lower than the temperature of the blood.

4. The system of claim 2 wherein said temperature of said solution is approximately room temperature.

5. The system of claim 1 wherein said solution is a saline solution.

6. The system of claim 3, wherein said change in the thermal energy level of the coronary blood stream is modulated by the pulsatile nature of the coronary blood stream from the aorta, generating cyclic thermal changes of a wavy character as the relatively warmer coronary blood stream mixes with said steady state, slow infusion of said solution; said wavy character of temperature changes coincides with the phasic stages of each cardiac cycle, presenting a pattern similar to a rectified sine waves; and said temperature sensors detect in sequence and within a short time period the phase shift between successive waves generated by said cyclic thermal changes, thereby producing values for the transit time of blood passing between said temperature sensors, such values being inversely proportional to the peak velocity of blood flow during a single cardiac cycle; as well as to average peak velocity through several successive cardiac cycles.

7. The guidewire of claim 1, wherein each of said temperature sensors comprises a thermocouple measuring junction, each of which is connected by conductive paths to respective sleeve electrodes mounted over the proximal 5–15 cms of said guidewire shaft.

8. The guidewire of claim 7, wherein said conductive paths are in the form of insulated copper and constantan wires, or wires of other metals and alloys of the type used as temperature sensors.

9. The guidewire of claim 7, wherein said sleeve electrodes are externally connectable by extension cables to respective reference junctions for each of said temperature sensors, and means are provided for maintaining each reference junction at a constant temperature.

10. The guidewire of claim 6, wherein said sleeve electrodes are connectable to an external monitoring system comprising:
   a separate thermocouple amplifier for each of said temperature sensors, said amplifiers monitoring the time of onset and offset of changes in said thermal energy levels in the coronary blood stream;
   means for presenting said separate thermocouple amplifiers output data including a programmed microprocessor and a fast sweep, color coded digital monitor or a printer.

11. The guidewire of claim 10, wherein said external monitoring system translates readings of the moving fluid's interphasic transit time into digital real-time values of peak coronary blood velocity over the segment of interest of the coronary artery during a single cardiac cycle.

12. A method for measuring coronary blood velocity using the system of claim 11 including the step of making several measurements of average peak velocity through normal, stenotic and post-stenotic segments of the coronary artery by moving said guidewire upstream and downstream in the coronary artery over normal and diseased segments.

13. The method of claim 12 wherein the mean flow velocity through said diseased segments is determined at basal conditions, during induced coronary hyperemia, or before, during and after coronary intervention procedures.

14. The method of claim 12, wherein reversed direction of blood flow is detected by reversed sequence of colors displayed on said color coded monitor.

15. The method of claim 12 wherein room temperature saline solution is infused into a coronary artery and, after said infusion of room-temperature saline solution is stopped, qualitative indications of transmyocardial microvascular velocity are obtained from the rate of return from said transient temperature drop to the normal coronary blood temperature level.

16. A method of measuring the velocity of coronary blood flow using the system of claim 1, said method comprising the steps of:
   introducing a steady state infusion of room temperature, miscible solution that is diluted and carried into the coronary blood stream in order to generate a thermal indicator by lowering the normal coronary blood temperature by a fraction of a degree centigrade;
   detecting the wavy-patterned temperature oscillations generated by the admixture of said room temperature infusion of solution with the pulsatile warmer blood flowing from the aorta, with its large diastolic and small systolic components, by means of said equally spaced temperature sensors placed sequentially along said distal segment of a coronary intervention guidewire that is introduced at a downstream site within a coronary artery;
   calculating the time lapse between phase shifts of said wavy-patterned temperature oscillations to provide values for the transit time of blood passing between said temperature sensors, said values being inversely proportional to the peak velocity of blood flowing in the coronary artery during a single cardiac cycle, as well as to the average peak velocity through several successive cardiac cycles recorded during the procedure; and,
   supplying said values via cables external to said guidewire and connected to a monitoring system that includes amplifiers, a fast-sweep color-coded monitor and a microprocessor capable of translating said values for the transit time of blood passing between said thermal sensors into digital real-time values for the average velocity of blood flowing in the coronary artery, at basal conditions, during induced hyperemia, and during and after coronary intervention procedures to enable a medical person to evaluate their outcome.

17. A method for measuring the velocity of blood flow in the coronary blood vessel system comprising the steps of:
   providing a guidewire having at least two temperature sensors mounted along a distal segment of said guidewire, said temperature sensors being disposed at equally spaced intervals over said distal segment of said guidewire;
   inserting said guidewire into a coronary blood vessel;
   changing the thermal energy level of the coronary blood streams by introducing a slow infusion of solution, having a temperature different than the temperature of the blood and being miscible with blood, into the coronary blood vessel as it flows in the coronary blood vessel, said infusion being introduced upstream at the coronary ostium and being carried downstream to induce a transient temperature difference in the coronary blood stream of a fraction of a degree centigrade;
   measuring the velocity of coronary blood flow with said temperature sensors by detecting in sequence the fluctuating thermal signal produced by the changing thermal energy level of the coronary blood stream as it flows in the vessel;
   said temperature difference being interrupted by the phasic oscillations generated by pulsatile blood flow entering from the aorta; and,
   measuring the time interval between said phasic oscillations by detecting in sequence with each one of said thermal sensors the pattern of temperature fluctuation of the blood at different locations in the blood vessel, as it flows in the coronary blood vessel, and for producing a value for said time interval which is indicative of the velocity of the blood flow in the coronary blood vessel.

18. The method of claim 17 wherein said solution is a saline solution at room temperature.

19. The method of claim 17 wherein said solution is at a temperature lower than the temperature of the blood.

20. The method of claim 17 further including the steps of:
   calculating the time lapse between phase shifts of said wavy-patterned temperature oscillations to provide values for the transit time of blood passing between said temperature sensors, said values being inversely proportional to the peak velocity of blood flowing in a coronary artery during a single cardiac cycle, as well as to the average peak velocity through several successive cardiac cycles recorded during the procedure; and, supplying said values via cables external to said guidewire and connected to a monitoring system that includes amplifiers, a fast-sweep color-coded monitor and a microprocessor capable of translating said values for the transit time of blood passing between said thermal sensors into digital real-time values for the average velocity of blood flowing in the coronary artery, at basal conditions, during induced hyperemia, and during and after coronary intervention procedures to enable a medical person to evaluate their outcome.

* * * * *